United States Patent [19]
Reed

[11] Patent Number: 5,746,997
[45] Date of Patent: May 5, 1998

[54] RADIOHALOGENATION OF OLIGONUCLEOTIDES VIA TRIALKYLSTANNYLARYL CONJUGATES

[75] Inventor: Michael W. Reed, Seattle, Wash.

[73] Assignee: Epoch Pharmaceuticals, Inc., Bothell, Wash.

[21] Appl. No.: 720,624

[22] Filed: Oct. 2, 1996

[51] Int. Cl.$^6$ .......................... A61K 51/00; A61M 36/14
[52] U.S. Cl. ...................... 424/1.73; 424/1.11; 424/1.65; 536/124
[58] Field of Search ...................... 424/1.11, 1.37, 424/1.65, 1.73, 9.1, 1.69; 536/1.11, 122, 124, 125, 126

[56] References Cited

U.S. PATENT DOCUMENTS 5,419,966  5/1995  Reed et al. .............................. 428/406
5,512,667  4/1996  Reed et al. .

FOREIGN PATENT DOCUMENTS 0198207  10/1986  European Pat. Off. .

OTHER PUBLICATIONS

Panyutin, I.G., et al. (1994) "Sequences-specific DNA double-strand breaks induced by triplex forming $^{125}$I labeled oligonucleotides" *Nucleic Acids Res.* 22, 4979.

Kassis, A. I., et al., (1987) "Therapeutic implications of auger-emitting radionuclides", *Radionuclides in Therapy*, (Spencer, R.P. et al., Ed.) pp. 120–134, (CRC Press, Inc., Boca Raton, FL).

Dewanjee, M.K., et al. (1991), "Development of sensitive radioiodinated anti-sense oligonucleotide probes by conjugation technique", *Bioconjugate Chem.*, 2/4: 195–200.

Fontanel, M.L., et al., (1993) "Synthesis and use of 4-hydroxyphenyl derivatized phosphoramidites in the selective radioiodination of oligonucleotide probes", *J. Lab. Comp. and Radiopharm*, 33/8: 717–724.

Wilbur, D.S., (1992) "Radiohalogenation of proteins: an overview of radionuclides, labeling methods, and reagents for conjugate labeling", *Bioconjugate Chem.* 3/6: 433–470.

Wilbur, D.S., et al., (1989) "Development of a stable radioiodinating reagent to label monoclonal antibodies for radiotherapy of cancer", *The Journal of Nuclear Medicine*, 30:216–226.

Hylarides, M.D., et al., (1991) "Preparation and in vivo evaluation of an N-(p-[$^{125}$I]Iodophenethyl)maleimide-antibody conjugate", *Bioconjugate Chemistry*, 2:435–440.

*Primary Examiner*—John Kight
*Assistant Examiner*—Dameron Jones
*Attorney, Agent, or Firm*—Klein & Szekeres, LLP

[57] ABSTRACT

Halogenated oligonucleotides and particularly radiohalogenated oligonucleotides are prepared by reacting a modified oligonucleotide with a trialkylstannylaryl reagent, such as an active ester of 4-(tri-n-butyl)benzoic acid. The modified oligonucleotide has a reactive group, such as an NH$_2$ group, covalently attached to a terminal phosphate or to a heterocyclic base, which reacts with the trialkylstannylaryl reagent to provide a trialkylstannylaryl-ODN conjugate. The trialkylstannyl group of the trialkylstannylaryl-ODN conjugate is rapidly replaced by halogen upon treatment with electrophilic halogen, such as I$^+$, that is formed when a halogen salt is treated with an oxidizing agent. The trialkylstannylaryl-ODN conjugate is significantly more lipophilic than the halogenated ODN and is readily separated from the halogenated ODN by simple reverse phase column chromatography. The method is especially suitable to introduce radioactive iodine into ODNs and yields the first known ODN labeled with essentially isotopically pure $^{123}$I.

30 Claims, No Drawings

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( i x ) FEATURE:
        ( A ) NAME/KEY: modified_base
        ( B ) LOCATION: 1
        ( D ) OTHER INFORMATION: /note="hexylamine tail"

( i x ) FEATURE:
        ( A ) NAME/KEY: modified_base
        ( B ) LOCATION: 15
        ( D ) OTHER INFORMATION: /note="hexanol tail"

( x i ) SEQUENCE DESCRIPTION: SEQ ID NO:1:

AACGTTGAGG GGCAT                                                  15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( i x ) FEATURE:
        ( A ) NAME/KEY: modified_base
        ( B ) LOCATION: 6
        ( D ) OTHER INFORMATION: /note="uracil modified with a covalently bonded 3-amino(propyl) group in the 5 position"

( i x ) FEATURE:
        ( A ) NAME/KEY: modified_base
        ( B ) LOCATION: 15
        ( D ) OTHER INFORMATION: /note="hexanol tail"

( x i ) SEQUENCE DESCRIPTION: SEQ ID NO:2:

AACGTUGAGG GGCAT                                                  15

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( i x ) FEATURE:
        ( A ) NAME/KEY: modified_base
        ( B ) LOCATION: 1
        ( D ) OTHER INFORMATION: /note="hexylamine tail attached to a 4-(tri-n- butyltin)benzoyl group"

( i x ) FEATURE:
        ( A ) NAME/KEY: modified_base
        ( B ) LOCATION: 15
        ( D ) OTHER INFORMATION: /note="hexanol tail"

( x i ) SEQUENCE DESCRIPTION: SEQ ID NO:3:

AACGTTGAGG GGCAT                                                  15

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( i x ) FEATURE:
        ( A ) NAME/KEY: modified_base
        ( B ) LOCATION: 6
        ( D ) OTHER INFORMATION: /note="uracil modified with a covalently bonded 3-amino(propyl) group to which a 4-(tri-n- butyltin)benzoyl group is attached"

( i x ) FEATURE:
        ( A ) NAME/KEY: modified_base
        ( B ) LOCATION: 15
        ( D ) OTHER INFORMATION: /note="hexanol tail"

( x i ) SEQUENCE DESCRIPTION: SEQ ID NO:4:

AACGTUGAGG GGCAT                                  15

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( i x ) FEATURE:
        ( A ) NAME/KEY: modified_base
        ( B ) LOCATION: 1
        ( D ) OTHER INFORMATION: /note="hexylamine tail to which a 4-(iodo)- benzoyl group is attached"

( i x ) FEATURE:
        ( A ) NAME/KEY: modified_base
        ( B ) LOCATION: 15
        ( D ) OTHER INFORMATION: /note="hexanol tail"

( x i ) SEQUENCE DESCRIPTION: SEQ ID NO:5:

AACGTTGAGG GGCAT                                  15

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( i x ) FEATURE:
        ( A ) NAME/KEY: modified_base
        ( B ) LOCATION: 6
        ( D ) OTHER INFORMATION: /note="uracil modified with a covalently bonded 3-amino(propyl) group to which a 4-(iodo)- benzoyl group is attached"

( i x ) FEATURE:
        ( A ) NAME/KEY: modified_base
        ( B ) LOCATION: 15
        ( D ) OTHER INFORMATION: /note="hexanol tail"

( x i ) SEQUENCE DESCRIPTION: SEQ ID NO:6:

AACGTUGAGG GGCAT                                  15

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single ( D ) TOPOLOGY: unknown ( i x ) FEATURE:
    ( A ) NAME/KEY: modified_base
    ( B ) LOCATION: 1
    ( D ) OTHER INFORMATION: /note="hexylamine tail to which a
          4-(iodo)- benzoyl group is attached containing I-125"

( i x ) FEATURE:
    ( A ) NAME/KEY: modified_base
    ( B ) LOCATION: 15
    ( D ) OTHER INFORMATION: /note="hexanol tail"

( x i ) SEQUENCE DESCRIPTION: SEQ ID NO:7:

AACGTTGAGG GGCAT                                              15

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( i x ) FEATURE:
        ( A ) NAME/KEY: modified_base
        ( B ) LOCATION: 1
        ( D ) OTHER INFORMATION: /note="hexylamine tail to which a
            4-(iodo)- benzoyl group is attached containing
            I-123"

( i x ) FEATURE:
        ( A ) NAME/KEY: modified_base
        ( B ) LOCATION: 15
        ( D ) OTHER INFORMATION: /note="hexanol tail"

( x i ) SEQUENCE DESCRIPTION: SEQ ID NO:8:

AACGTTGAGG GGCAT                                              15

( 2 ) INFORMATION FOR SEQ ID NO:9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( i x ) FEATURE:
        ( A ) NAME/KEY: modified_base
        ( B ) LOCATION: 6
        ( D ) OTHER INFORMATION: /note="uracil modified with
            covalently bonded 3-amino(propyl) group attached
            to 4-(iodo)- benzoyl group containing I-125"

( i x ) FEATURE:
        ( A ) NAME/KEY: modified_base
        ( B ) LOCATION: 15
        ( D ) OTHER INFORMATION: /note="hexanol tail"

( x i ) SEQUENCE DESCRIPTION: SEQ ID NO:9:

AACGTUGAGG GGCAT                                              15

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( i x ) FEATURE:
        ( A ) NAME/KEY: modified_base
        ( B ) LOCATION: 6
        ( D ) OTHER INFORMATION: /note="uracil modified with covalently bonded 3-amino(propyl) group attached
to 4-(iodo)- benzoyl group containing I-123"

( i x ) FEATURE:
  ( A ) NAME/KEY: modified_base
  ( B ) LOCATION: 15
  ( D ) OTHER INFORMATION: /note="hexanol tail"

( x i ) SEQUENCE DESCRIPTION: SEQ ID NO:10:

AACGTUGAGG GGCAT   15

( 2 ) INFORMATION FOR SEQ ID NO:11:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

CCAGCAGCCT CCCGCGACGA TGCCCCTCAA CGTTAGCTTC AC   42

( 2 ) INFORMATION FOR SEQ ID NO:12:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

CCAGCAGCCT CCCGCGACGT ATCTAGGGGG ACACAGCTTC AC   42

RADIOHALOGENATION OF OLIGONUCLEOTIDES VIA TRIALKYLSTANNYLARYL CONJUGATES

BACKGROUND OF THE INVENTION

1. Field of the Invention

The present invention is in the field of radionuclide labeled oligonucleotides and in the field of synthesizing radionuclide labeled oligonucleotides. More particularly, the present invention is in the field of synthesizing radiohalogenated oligonucleotide probes.

2. Brief Description of the Prior Art

Synthetic oligonucleotides (ODNs) are widely used in the state-of-the-art as probes for identification of specific gene sequences from various organisms, in the diagnostics of human genetic diseases, as well as in the development of antisense, and antigene therapy. Radionuclide labeled ODNs are well known in the art not only as readily detactable probes, but also as agents which when hybridized with a complementary strand may cause cleavage of DNA and RNA targets both in vitro and in vivo.

Radioactive phosphorous (i.e. $\gamma 32$ P) and radioactive iodine isotopes (i.e. $^{125}$I) labeled ODNs have been widely used in the prior art. Iodine isotope $^{125}$I has a half life of 60 days. Another isotope of iodine, $^{123}$I has a half life of 13.2 hours. When hybridized with a complementary pair, ODNs having the $^{125}$I isotope are known to cause cleavage of the double stranded nucleic acid, but there is no data in the prior art whether or not similar cleavage would occur upon hybridization with $^{123}$I bearing ODNs. Initially, the $^{123}$I isotope was introduced into ODNs by iodination of the ODN, with the result that iodine is "randomly" introduced into the cytosine bases of the ODN. Another more satisfactory procedure for introducing iodine, and particularly the radioactive iodine isotope $^{125}$I into ODNs, is described in EPO patent application O 198 207 A1, published on Oct. 22, 1986. The latter procedure has been developed for use in conjunction with automated ODN synthesizers, and involves the preparation of an ODN having a primary amine function attached to one or more bases. The ODN bearing the amino function or functions is then reacted with a reagent that introduces in the ODN, with a carboxamide linkage, a moiety including an aromatic phenol or like group which is susceptible to electrophilic substitution. The phenolic moiety is iodinated by treatment with an iodide salt carrying labeled iodine, in the presence of a mild oxidizing agent, such as chloramine T. In accordance with this prior art method the iodinated product must be separated from the non-iodinated precursor by tedious procedures, such as high pressure liquid chromatography (HPLC).

Further background to the present invention is provided in the following publications:

Panyutin, I. G. and Neumann, R. D. (1994) Sequence-specific DNA double-strand breaks induced by triplex forming $^{125}$I labeled oligonucleotides. *Nucleic Acids Res.* 22, 4979;

Kassis, A. L., Adelstein, J., and Bloomer, W. D. (1987) Therapeutic Implications of Auger-emitting radionuclides. *Radionuclides in Therapy* (Spencer, R. P. et al., Ed.) pp 120–134, CRC Press, Inc., Boca Raton, Fla.;

Dattagupta, N., and Knowles, W.; EP 80198207; Dewanjee, M. K., Ghafouripour, A. K., Werner, R. K., Serfini, A. N., and Sfakianakis, G. N. (1991) Development of sensitive radioiodinated anti-sense oligonucleotide probes by conjugation technique. *Bioconjugate Chem.* 2, 195;

Fonanel, M. L., Bazin, H., Roget, A., and Teole, R. (1993) Synthesis and use of 4-hydroxyphenyl derivatized phosphoramidites in the selective radioiodination of oligonucleotide probes. *J. Lab. Comp. and Radiopharm.* 33, 717, and Wilbur, D. S. (1992) Radiohalogenation of proteins: an overview of radionuclides, labeling methods, and reagents for conjugate labeling. *Bioconjugate Chem.* 3, 433.

SUMMARY OF THE INVENTION

In accordance with the present invention a modified ODN is first obtained by state-of-the-art techniques, for example on an automated ODN synthesizer. The ODN bears one or more groups which are capable of reacting with an activated form of an aromatic or vinylic trialkylstannyl compound. The modified ODN is reacted with the activated aromatic or vinylic trialkylstannyl compound to provide ODN derivatives bearing the aromatic or vinylic trialkylstannyl moiety or moieties. The reaction between the modified ODN and the activated form of the aromatic or vinylic trialkylstannyl compound is one between nucleophilic and electrophilic centers where either center can be attached to either one of the reactants.

The aromatic or vinylic trialkylstannyl moieties are readily and rapidly demetallated and converted to iodo or other halogen substituted derivatives by reaction with electrophilic $I^+$, $Br^+$, $Cl^+$ or $F^+$, that is, by reaction with a halide salt (such as NaI) in the presence of a mild oxidizing agent. When this reaction is conducted with a radioactive halogen isotope, such as $^{123}$I, $^{125}$I, $^{131}$I, $^{77}$Br, $^{80m}$Br, $^{18}$F, or $^{211}$At then the ODN bearing the trialkylstannyl moieties is advantageously used in excess so as to ensure maximum utilization of the radioactive halogen (preferably iodine) component. The modified ODN bearing the iodine or other halogen substituted aromatic or vinylic moiety is readily separated by reverse phase chromatography from the significantly more lipophilic ODN bearing the trialkylstannyl group or groups. The separation is effective and practically complete without an elaborate procedure even when the ODN bearing the trialkylstannylaryl groups is in large excess relative to the halogenated ODN. The process is suitable for introducing all radioactive halogens, and particularly $^{125}$I isotope as well as the much shorter half-lived $^{123}$I isotope into ODNs, and can be performed without utilizing a non-radioactive halogen carrier. The process of the invention results in the first synthesis of essentially isotopically pure $^{123}$I labeled ODNs. Hybridization studies showed that the $^{123}$I label did not adversely effect sequence specificity of the ODN probe.

DETAILED DESCRIPTION OF THE INVENTION

The present invention relates to a process for introducing radioactive iodine (or other halogen) isotopes into oligonucleotides (ODNs). Except to the extent that the ODN must include one or more reactive groups which are utilized in the process, the nature of the ODN is not critical from the standpoint of the present invention. Thus, the process of the invention can be applied to ODNs containing the naturally occurring 2-deoxyribonucleotides (oligodeoxyribonucleotides), to ODNs containing the naturally occurring ribonucleotides (oligoribonucleotides) and to ODNs which contain sugars other than 2-deoxyribose and ribose, as well as to ODNs containing 2-deoxyribose, ribose and other sugars in other than the "natural" β glycosidic configuration. The ODNs to which the process of the present invention is applied may also contain one or more heterocyclic bases (or base analogs such as "virtual nucleotides") other than the major naturally occurring components of deoxyribonucleic acids and ribonucleic acids. Chemistry pertaining to nucleosides, nucleotides and ODNs including ribose, 2-deoxyribose, derivatives of ribose and 2-deoxyribose, as well as other sugars in both β and α anomeric configurations, as well as various heterocyclic aglycon bases, is well developed in the art and need not be described here. The number of nucleotide units in the ODNs to which the process of the present invention is applied is also not critical. Preferably, however, the process of the invention is applied to ODNs having approximately 2 to 200 nucleotides.

In addition to possibly having modified sugars and or modified heterocycles, the ODNs to which the process of the present invention is applied may also have a tail attached to either or both ends of the molecule. Except when the tail participates in the reaction involved in the novel process, the nature of the tail or tails is not critical, and may include virtually any tail moiety which is known in the state of the art. Such tail moieties include alkyl groups, hydroxyalkyl groups, various lipophilic groups, including cholesterol and other steroids, and aminoalkyl groups. Further description of various tail molecules as well as of a method for synthesizing ODNs with various tail molecules, including hydroxyalkyl and aminoalkyl tails, is found in U.S. Pat. Nos. 5,419,166 and 5,512,667, the specifications of which are incorporated herein by reference. As it will be seen below, when the tail of the ODN terminates in a reactive group, particularly in an amino group, then the tail is particularly well suited for participating in the preferred sequence of the invention.

In accordance with the invention radioactive iodine substituent is introduced into an ODN, modified as described below, by utilizing a trialkylstannylaryl reagent of Formula 1, or of Formula 2.

  Formula 1

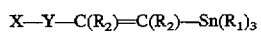  Formula 2

In Formulas 1 and 2 $R_1$, is an alkyl or cycloalkyl group having 1 to 10 carbons;

X and Y jointly represent a linker arm combined with a reactive group that is capable of joining the moiety of Formula 1 or of Formula 2 with (a) a nucleophilic group such as an amine, or thiol (b) alternatively X and Y jointly represent a linker arm combined with a reactive group that is capable of joining the moiety of Formula 1 or of Formula 2 with an electrophilic group such as an alkylating, sulphonylating, or acylating group or with an isothiocyanate or isocyanate.

Regarding the aryl groups to which the trialkylstannyl (—Sn($R_1$)$_3$) group is attached, presently preferred is a phenyl group without any optional $R_3$ groups. The presently preferred $R_1$ group is n-butyl, so that the preferred moieties in accordance with Formula 1 include a tributylstannylphenyl group to which the X—Y—group is preferably attached in 1,4 (para) position.

The function of the compounds of Formula 1 or of Formula 2 in accordance with the present invention is to react with one or more reactive groups incorporated either internally or at the terminus of the modified ODN, where the reactive group and the moiety attaching it to the ODN is jointly represented by —X'—Y'. The moiety —X'—Y' is described in the same manner as the —X—Y moiety of Formula 1 or of Formula 2. In other words, the —X—Y moiety of the reagent of Formula 1 or of Formula 2 and the —X'—Y' moiety of the modified ODN react with one another in a reaction involving nucleophilic and electrophilic centers to covalently link one or more trialkylstannylaryl or trialkylstannyl vinyl groups to the ODN. As noted above, the trialkylstannylaryl or trialkylstannyl vinyl group or groups may be linked to the ODN internally, that is to a heterocyclic base of the ODN, or through a tail attached to the 3' or 5' terminal phosphate group of the ODN. ODNs having the —X'—Y' groups attached either internally or to a terminal phosphate as a "tail" can be jointly represented by Formula 3 where p is an integer having the value of 1 to approximately 30 but less than the number of nucleotides in the ODN of Formula 3 itself.

ODN—(Y'—X')$_p$  Formula 3

In the situation where the trialkylstannylaryl or trialkylstannyl vinyl group is linked to a "tail" attached to one of the terminal phosphates of the ODN, then the ODN with the "tail" can be prepared in accordance with procedures known in the art, for example in accordance with the methodology described in the above-cited U.S. Pat. Nos. 5,419,166 and 5,512,667. Whereas "tail" groups having the above described reactive groups are suitable for practicing the invention, tails having a terminal amino group (aminoalkyl tail) are particularly preferred.

State-of-the-art synthetic methodology can also be employed for the preparation of ODNs having an internally linked —Y'—X' group, as intermediates for the preparation of ODNs where the the trialkylstannylaryl or trialkylstannyl vinyl group or groups are linked to a heterocyclic base. Generally speaking, internal modification of the ODN so as to obtain the intermediates of Formula 3 proceeds by first obtaining a nucleoside having the desired —Y'—X' group attached to the heterocyclic base. The —Y'—X' group may be protected, if necessary, by synthetic methodology well known in the art, and the resulting modified nucleoside is incorporated into an ODN in accordance with standard methodology, for example on an automated ODN synthesizer. The ODN intermediate of Formula 3 may include a 5-(aminoalkyl)-2'-deoxyuridine or a 5-(aminoalkyl)-uridine component, which can be obtained in accordance with the teaching of Meyer et al., *J. Am. Chem. Soc.* 1989 111, 8517. This component is then used in routine oligonucleotide synthesis to obtain a preferred embodiment of an ODN in accordance with Formula 3 where the —Y'—X' group is (—CH$_2$)$_3$NH$_2$ or like aminoalkyl group. More generally, 5-substituted 2'-deoxyuridines and uridines can be obtained by an adaptation of the general procedure of Robins et al. *Can. J. Chem.*, 60: 554 (1982); *J. Org. Chem.*, 48: 1854 (1983)). In accordance with this methodology, the palladium-mediated coupling of a substituted 1-alkyne to 5-iodo-2'-deoxyuridine gives an acetylene-coupled product. The acetylenic dUrd analog is reduced, with Raney nickel for example, to give the saturated compound, which is then used for direct conversion to a reagent for use on an automated ODN synthesizer. Examples of reagents which can be coupled to 5-iodo-2'-deoxyuridine (or to 5-iodouridine) in accordance with this scheme are HC≡CCH$_2$OCH$_2$CH$_2$N(CO)$_2$C$_6$H$_4$ (phthalimidoethoxypropyne), HC≡CCH$_2$OCH$_2$CH$_2$NHCOCF$_3$ (trifluoroacetamidoethoxypropyne), HC≡CCH$_2$N(CO)$_2$C$_6$H$_4$ (phthalimidopropyne) and HC≡CCH$_2$NHCOCF$_3$ (trifluoroacetamidopropyne), In these examples the nucleosides are incorporated into the desired ODN, and a free terminal amino group can be obtained after removal of the respective phthalic or trifluoroacetyl blocking groups. Other examples of nucleoside components to which the —Y'—X' moiety is attached, so as to provide after oligonucleotide synthesis, an ODN intermediate of Formula 3, are 4-aminopyrazolo[3,4-d]pyrimidine derivatives. The general structure of these derivatives is shown below in Formula 4.

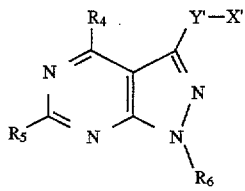

Formula 4

—Y'—X' are as described above. $R_6$ represents a sugar moiety as described above, preferably ribose or 2-deoxyribose, and $R_4$ and $R_5$ independently are H, $OR_7$, $SR_7$, $NHOR_7$, or $NH_2$ where $R_7$ is H or $C_{1-6}$ alkyl. These compounds can be made from 3,4-disubstituted and 3,4,6-trisubstituted pyrazolo[3,4-d]pyrimidines, in accordance with the teaching of Kobayashi in Chem. Phar. Bull. 21:941–951 (1973) which is incorporated herein by reference.

Still further examples of nucleoside components to which the —Y'—X' moiety is attached, so as to provide, after oligonucleotide synthesis, an ODN intermediate of Formula 3 are known in the chemical literature. Several of these modified nucleosides are available commercially in a form already activated for synthesis in an automated ODN synthesizer. Commercial sources for these reagents include Glen Research (Sterling Virginia) and Clontech Laboratories Inc. (Palo Alto Calif.). In addition, "virtual nucleotide" reagents which maintain the sugar-phosphate backbone and include the —Y'—X" group (such as a group terminating in a primary amine function) are also known in the literature and some are available commercially. Such "virtual nucleotide" components may also be included in the ODN of Formula 3.

After reaction between the oligonucleotide of Formula 3 and the trialkylstannyl reagent of Formula 1 or of Formula 2, a trialkylstannyl ODN conjugate of Formula 5 or of Formula 6 is obtained.

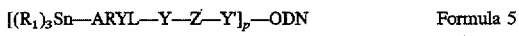

Formula 5

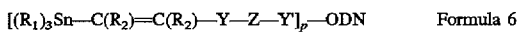

Formula 6

In Formulas 5 and 6 the symbols $R_1$, $R_2$, p and ARYL are defined as above. Z is a moiety or group that is formed as a result of the reaction between the electrophilic and nucleophilic moieties represented by the symbols X and X' in Formulas 1–3. Examples for the Z moiety or linkage are:

(1) —CO—NH—;
(2) —NH—CO—NH—;
(3) —NH—CS—NH—;
(4) NH—CO—CH$_2$—S—, and

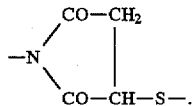

(5)

It should be apparent to those skilled in the art in light of the foregoing that the symbols Y and Y' represent linkers between the reactive groups X and X'. Because the linkers themselves do not participate in the reaction in which the Z moiety is formed, the linkers Y and Y' may be alkyl, or aryl groups, or may themselves include one or more amide, ether, thioether or ester function, as well as unsaturated carbon to carbon linkages and aromatic groups. Generally speaking the total length of the two linkers Y or Y' should not exceed the approximate overall length of a normal alkyl chain of 25 carbons. One or both of the linkers may even be absent, for example when 5-amino-2'-deoxyuridine or 5-aminouridine is incorporated in the ODN, and also in the example provided below for the preferred embodiment of the trialkylstannylphenyl reagent within the scope of Formula 1.

Referring to other examples obtained by coupling phthalimidoethoxypropyne, trifluoroacetamidoethoxypropyne, phthalimidopropyne, or trifluoroacetamidopropyne to 5-iodo-2'-deoxyuridine, followed by saturation of the triple bond, the resulting linker moiety Y' (attached to the ODN) is $-(CH_2)_3O(CH_2)_2-$ and $-(CH_2)_3-$ respectively. The presently most preferred linker group Y' for linking internally to the ODN is $-(CH_2)_3-$ (n-propylene), which is preferably attached to the 5 position of 2' deoxyuridine or uridine in the ODN. The presently most preferred linker group Y' for linking to the 5' terminal of the ODN is $-(CH_2)_6-$ (n-hexylene). A presently highly preferred example for the linker Y attached to the trialkylstannylphenyl moiety in the 1,4 (para) position is $(CH_2)_q$ where q is an integer, most preferably zero. Thus, the foregoing and other examples for the linkers Y and Y' can be generalized by the formulas $-(CH_2)_q-$, $-(CH_2)_r-C_6H_4-$, $-(CH_2)_sO(CH_2)_t-$ where q is an integer between 0 and 20, r is an integer between 0 and 20, s is an integer between 1 and 20, and t is an integer between 1 and 20. This generalization, however, should not be considered exclusive, because as noted above suitable linkers may include ester, amide, and other linkages and heterocyclic moieties, for example such as the one shown in Reaction Scheme 1 as part of Compound A.

Based on the exemplary structures (1) through (5) shown above, the moiety Z in the trialkylstannyl ODN conjugates of Formula 5 or of Formula 6 is (1) an amide linkage which can be obtained by reaction between an active ester or other activated form of carboxylic acid (such as an acid halide) and a primary amine. Presently preferred in the process of the present invention is a primary amine for the X' group (attached to the ODN of Formula 3) and an active ester for the X group attached to the trialkylstannyl reagent of Formula 1 or of Formula 2. A preferred example for the active ester is formed from 4-trialkylstannylbenzoic acid with N-hydroxysuccinimide. This reagent can be obtained from methyl 4-bromobenzoate in accordance with the literature procedure of Wilbur et al. *The Journal of Nuclear Medicine* 30, 2 p 217 (1989), and its preparation is also described in the detailed experimental section below.

Reaction Scheme I

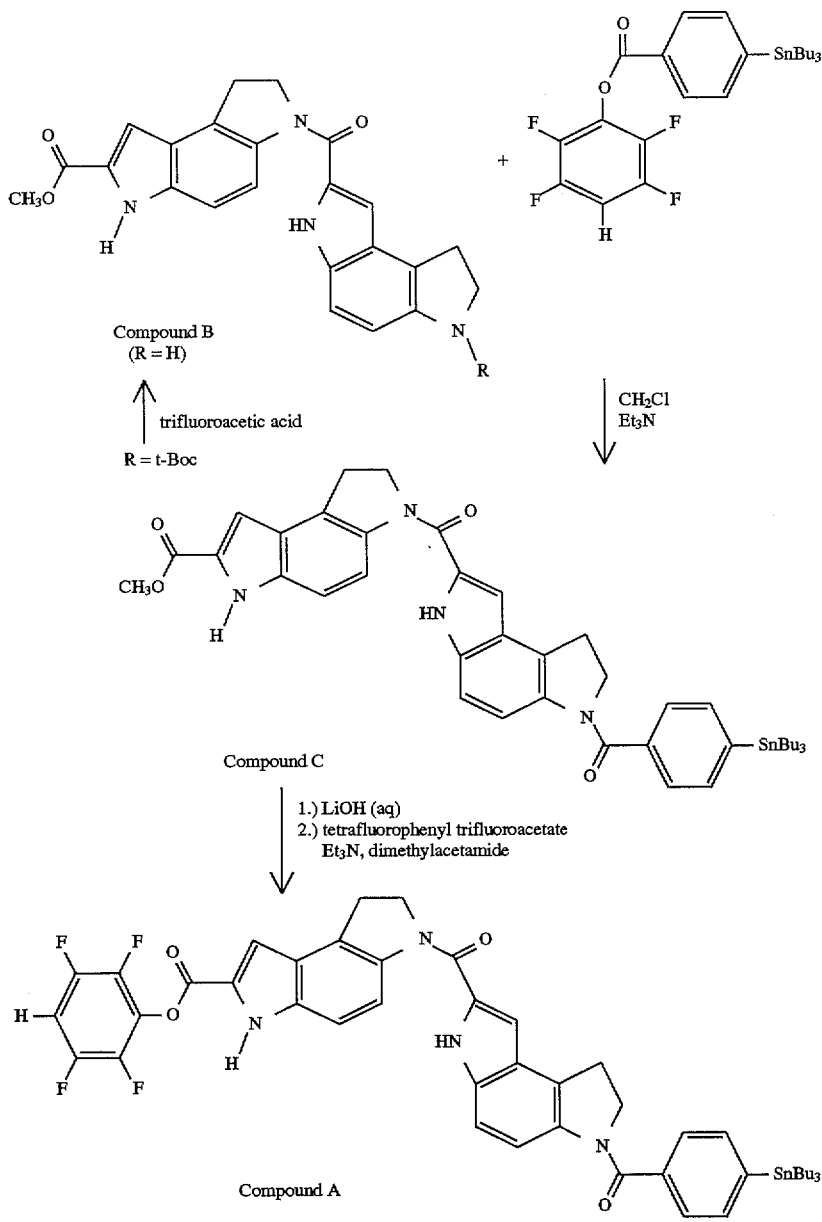

In Compound A (Reaction Scheme 1) the two pyrrolo[3,2-e]indol moieties serve as the linker Y, and the active ester is formed with 2,3,5,6-tetrafluorophenol. Compound A can be obtained as shown in Reaction Scheme 1 starting with the known tertiary-butylcarbonyloxy (t-Boc) protected derivative of 1,2-dihydro-3H-pyrrolo[3,2e]indole-7-carboxylate dimer methyl ester that is available according to the literature method of Boger et al. *J. Org. Chem.* 1987, 52, 1521–1530, incorporated herein by reference. The synthetic steps leading from this t-Boc protected derivative through 1,2-dihydro-3H-pyrrolo[3,2-e]indole-7-carboxylate dimer methyl ester (Compound B) to Compound A (which is a reagent within the scope of Formula 1) are indicated in the scheme, and are also described in the detailed experimental section of the present application for patent.

The moiety Z in accordance with structure (2) is a substituted urea, that can be obtained by reaction between a primary amine and an isocyanate. The moiety Z in accordance with structure (3) above is a thiourea that can be obtained by reaction between a primary amine and an isothiocyanate. In these examples the primary amine and isocyanate or isothiocyanate functions respectively represent the X and X' groups in Formulas 1–3. Preferably the primary amine is attached to the ODN and the isocyanate or isothiocyanate is attached to the trialkylstannylaryl or trialkylstannylvinyl group.

The moiety Z in accordance with structure (4) is formed by reacting a primary amine, such as one attached to the ODN, with an activated ester, anhydride or halide of an α-halogenated carboxylic acid, for example with the anhydride of iodoacetic acid, followed by reaction with a thiol. Thus, in this example the thiol represents the reactive X group of Formula 1 or of Formula 2. In order to utilize the moiety Z of structure (4) it is advantageus to prepare an ODN having the exposed primary amine groups, and thereafter react the ODN with iodo acetic anhydride or like reagent. This is followed by coupling with a thiol containing trialkylstannyl reagent that is within the scope of Formula 1 or 2.

The moiety Z in accordance with structure (5) is the result of a reaction between a maleimide derivative and a thiol. For example, the thiol may be attached to the ODN so that in Formula 3 X' represents the SH group. The thiol is then reacted with the maleimide derivative of a trialkylstannylaryl compound, that can be obtained in accordance with the chemical literature. Specifically for the synthesis of trialkylstannylphenylethyl maleiimides see Hylarides et al. *Bioconjugate Chemistry* 1991 2, 435–440, incorporated herein by reference.

The reactions leading to the formation of compounds of Formula 5 and 6 are usually performed in a mixture of aqueous and organic solvents because the lipophilic trialkylstannyl reagents are poorly, if at all, soluble in water or aqueous buffers. Thus, for the reaction medium emulsions of aqueous borate buffer and tetrahydrofuran are preferred. In an alternative preferred mode the ODN is converted into the triethylammonium (or like) salt, and the reaction is conducted in dimethylsulfoxide (DMSO).

In the next step of the process of the invention the trialkylstannyl ODN conjugates of Formula 5 or of Formula 6 are reacted with an electrophilic halogen ($I^+$, $Br^+$, $Cl^+$, or $F^+$) which results in rapid demetallation of the stannyl derivatives, and replacement of the trialkylstannyl group with halogen. The reaction, shown in Reaction Scheme 2, results in halogenated ODNs of Formula 7 and Formula 8, respectively where $\Psi$ represents halogen.

Reaction Scheme 2

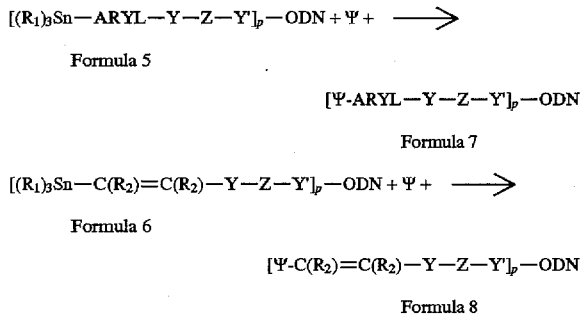

The halogenation—demetallation reaction shown in Reaction Scheme 2 is preferably performed in an aqueous or mixed aqueous and organic solvent (such as aqueous methanol) medium, with an appropriate halide salt providing the source of halogen, and in the presence of a mild oxidizing agent. Because the reaction is predominantly used for introduction of a radioactive halogen isotope, the halide salt contains the radioactive halogen. $Na^{123}I$ and $Na^{125}I$ serve as preferred examples for the introduction of radioactive iodine. Sodium or other soluble salts of radioactive bromine, and fluorine serve as examples for the introduction of other radioactive halogens. Examples of suitable mild oxidizing agents are sodium p-toluenesulfonchloramide (chloramine T), N-chlorosuccinimide, iodogen (1,3,4,6-tetrachloro-3α, 6α-diphenylglycoluril), immobilized iodogen (iodobeads) and dibromodimethylhydantoin.

As it is well understood by those skilled in the art, radioactive halogen salts, such as $Na^{123}I$ or $Na^{125}I$ are valuable, and ideally should be utilized fully in the demetallation—halogenation reaction. To this end, it is desirable to use an excess of the trialkylstannyl ODN conjugate of Formula 5 or of Formula 6 in the demetallation halogenation reaction relative to the radioactive halogen salt. In accordance with the present invention this is feasible, because the desired end product halogenated ODN of Formula 7 or of Formula 8 is readily separated from trialkylstannyl ODN conjugates, as well as from the other reagents used in the demetallation—halogenation reaction. More particularly, readily feasible isolation of the halogenated ODNs of Formula 7 or of Formula 8 is rendered possible by the large difference in lipophilicity between the trialkylstannyl ODN conjugates of Formula 5 or of Formula 6 and the halogenated ODNs of Formula 7 or of Formula 8. The trialkyl stannyl conjugates are significantly more lipophilic than the halogenated ODNs, and therefore can be readily separated on a reverse phase column, that is, a chromatographic column loaded with a hydrophobic adsorbent. Such columns and adsorbents are well known in the art, and are commercially available. A suitable adsorbent for this purpose that is used in the preferred embodiment of the process, is known as C-18 silica. It is a silica absorbent to which a lipophilic C-18 carbon chain has been covalently bonded. Another type of adsorbent for reverse phase columns is polystyrene-divinylbenzene copolymer which is also commercially available.

Separation of the reaction mixture and isolation of the desired halogenated ODNs of Formula 7 or of Formula 8 is performed on the reverse phase column by placing the reaction mixture on the column, and subsequently eluting the column with a gradually increasing concentration of water miscible organic solvent added to an aqueous base. The aqueous base or solvent is preferably triethylammonium acetate (TEAA) solution in water (approximately 0.1 Molar, buffered to pH 7.0). Alternatively 0.1 M sodium perchlorate solution, or 0.1 Molar lithium perchlorate solutions may also serve as examples. The organic eluent is preferably acetonitrile ($CH_3CN$), although other water-miscible organic solvents such as methanol, ethanol, acetone, or tetrahydrofuran may also serve as examples. Elution of the reaction mixture is typically commenced with a predominantly aqueous medium, such as 0.1M TEAA solution containing approximately 5% acetonitrile. The concentration of acetonitrile (or other organic solvent) is gradually raised during elution in a manner that the concentration of acetonitrile in the eluent reaches approximately 85% in approximately 40 minutes. Inorganic reactants including any unreacted halide salt, oxidizing agent as well as the "reduced form" of the oxidizing agent is usually eluted first; in one preferred example radioactive iodide salt was eluted in about 4 minutes. Iodinated (or otherwise halogenated) ODN of Formula 7 or of Formula 8 is eluted next; in the above noted example it comes off the column in approximately 12 minutes. Elution of the radioactive compounds can be readily monitored with a γ radiation detector. Because the trialkylstannyl ODN conjugates of Formula 5 or of Formula 6 are much more lipophilic, they are eluted from the column only significantly later, even when they are in large relative to the halogenated ODNs. In the above-noted example the trialkylstannyl ODN conjugates came off the column in approximately 30 minutes. For this reason clear and clean separation of the halogenated ODNs from the excess of trialkylstannyl ODN conjugates is obtained.

In a particularly advantageous and preferred embodiment of the process of the invention the desired halogenated ODNs of Formula 7 or of Formula 8 are obtained from a disposable syringe cartridge column that is filled with "reverse phase" polystyrene-divinyl-benzene-copolymer. Such cartridges are available commercially, for example from Glen Research (Sterling Va.). The cartridge (approximately ½" long) on which the reaction mixture is placed, is eluted with a succession of aqueous and organic solvent mixtures. Specifically, 0.1 Molar aqueous TEAA solution is used to wash off inorganic materials and oxidizing agents from the column. This is followed by 20% acetonitrile in approximately 0.1 Molar aqueous TEAA to elute essentially pure halogenated ODN. At that point, unless it is desired to also recover excess trialkylstannyl ODN conjugate of Formula 5 or of Formula 6 by elution with more concentrated organic solvent, the disposable column can be discarded. Alternatively, the column is discarded after recovery of the trialkylstannyl ODN conjugate that had been used in excess in the halogenation-demetallation reaction.

Ease of isolating the halogenated ODNs in accordance with the present invention is considered a major advantage in that in the prior art radiohalogenation processes complicated and tedious chromatographic procedures needed to be employed.

The radiohalogenated ODNs made in accordance with the process of the present invention can be utilized as radioactive probes in all types of processes and procedures where radioactive ODN probes are normally employed, for example in analytical and diagnostic procedures, forensics and gene mapping. Some of the radioactive ODNs made in accordance with the present invention, such as $^{125}$I labeled ODNs, are also effective as sequence specific cleaving agents; see for example the publication Martin et a., Science 213 21, 896 (1981), incorporated herein by reference. Because the process of the present invention can be performed rapidly, it makes it possible to prepare $^{123}$I labeled ODNs without any non-radioactive carrier. Up to the present invention due to the short half life of $^{123}$I, ODNs labeled with this isotope without any non-radioactive carrier have not been reported. Thus, as far as the present inventors are aware the present invention provides the first isotopically pure $^{123}$I labeled ODNs.

In connection with the preferred embodiment of the process of the present invention and as demonstration of the inventive process, a 15-mer ODN of SEQUENCE ID) No. 1 was prepared on an automated ODN synthesizer. This ODN has an n-hexylamine tail on its 5' end and a hexanol tail at its 3' end. Another 15-mer ODN of SEQUENCE ID No. 2 has a hexanol tail on its 3' end, and includes an internally modified 2'-deoxyuridine that carries a 3(amino) propyl group in its 5-position. The structures of the ODNs of SEQUENCE ID No. 1 and SEQUENCE ID No. 2 are shown below.

SEQUENCE ID No. 1

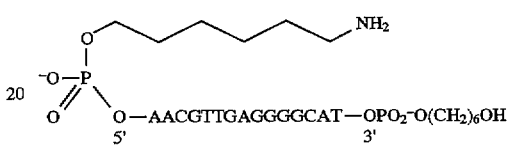

SEQUENCE ID No. 2

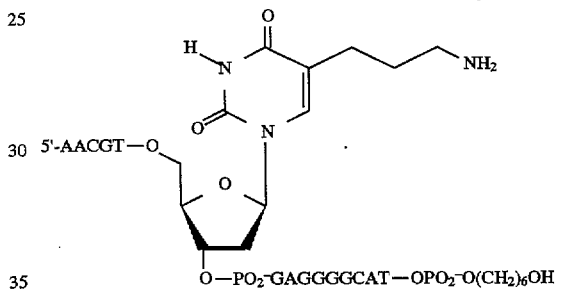

Each of these ODNs (SEQUENCE ED No. 1 and SEQUENCE ID No. 2) were reacted with N-hydroxysuccinimidyl-4-tri-(n-butyl)stannylbenzoate to provide ODNs identified as SEQUENCE ID No. 3 and SEQUENCE ID No. 4.

SEQUENCE ID No. 3

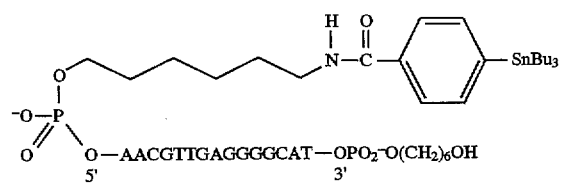

SEQUENCE ID No. 4

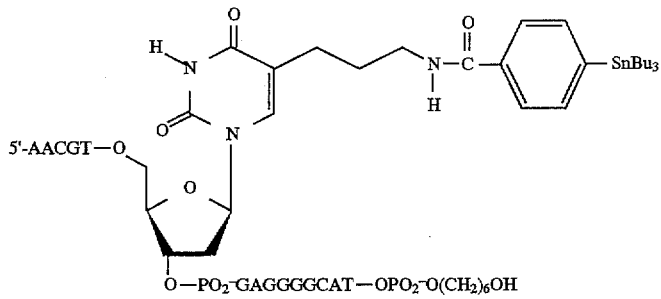

The ODNs of SEQUENCE ID No. 3 and of SEQUENCE ID No. 4 were reacted with non radioactive ($^{127}$I) sodium iodide in a borate buffer in the presence of chloramine T. The reactions were quenched after 5 minutes by addition of a reducing agent (sodium bisulfite). The non-radioactive iodinated ODNs which were isolated from the respective reactions by chromatography have SEQUENCE ID No. 5 and SEQUENCE ID No. 6, respectively, and are shown below.

The ODNs obtained in this manner were identical with (and co-eluted in chromatography) with the iodinated ODNs that were prepared through the trialkylstannyl method in accordance with the present invention.

By utilizing $^{125}$iodine and $^{123}$iodine containing sodium iodide (Na$^{125}$I and Na$^{123}$I) respectively, and using substantially the same procedure as described above, coupled with SEQUENCE ID No. 5

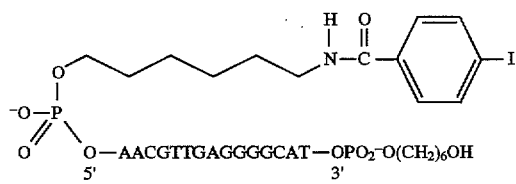

SEQUENCE ID No. 6

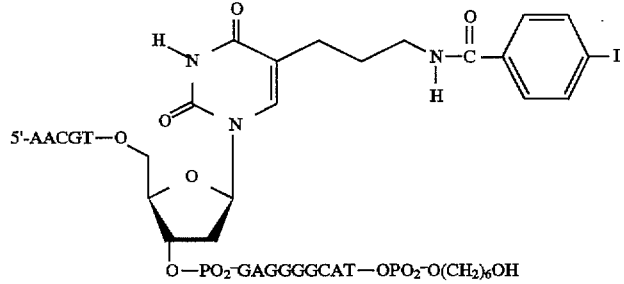

As proof of the respective structures of the iodinated ODNs of SEQUENCE ID No. 5 and of SEQUENCE ID No. 6, these same ODNs were also prepared by reacting the ODNs of SEQUENCE ID No. 1 and SEQUENCE ID No. 2, respectively, with non-radioactive 4-iodobenzoyl chloride.

purification on a short reverse-phase column, each of the tributylstannylphenyl ODN conjugates of SEQUENCE ID No. 3 and of SEQUENCE ID No. 4 can be converted to the corresponding radioiodine labeled ODNs, having SEQUENCE ID Nos. 7–10, shown below.

SEQUENCE ID No. 7

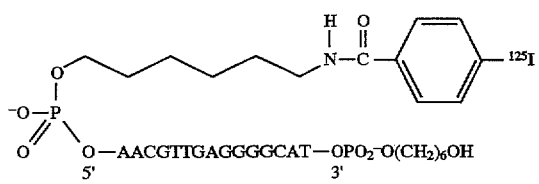

SEQUENCE ID No. 8

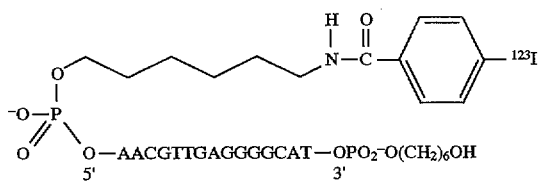

SEQUENCE ID No. 9

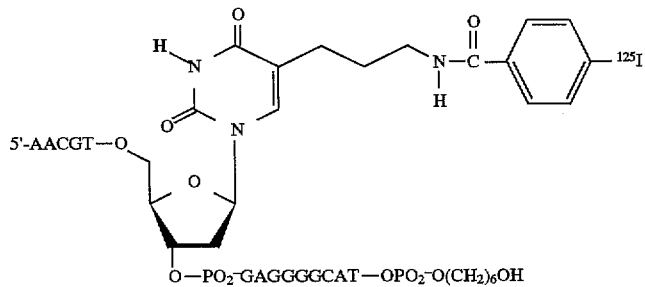

SEQUENCE ID No. 10

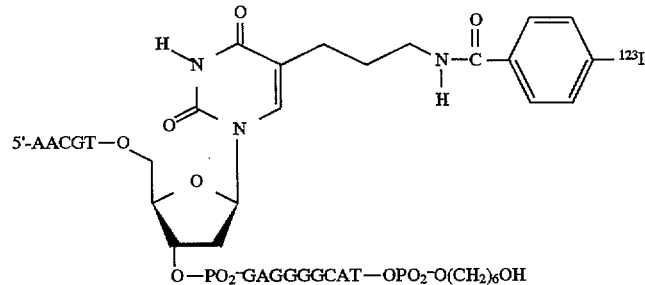

In order to conduct hybridization and thermal denaturation (melting temperature) studies, 42-mer ODNs of SEQUENCE ID No. 11 and SEQUENCE ID No. 12 were prepared. In the ODN of SEQUENCE ID No. 11 the underlined portion is complementary in the Watson Crick sense to the ODNs of SEQUENCE ID Nos. 1 and 2, and as the hybridization experiments conducted in accordance with the present invention proved, with the radioiodine labeled ODNs of SEQUENCE ID Nos. 5–10 as well. In the ODN of SEQUENCE ID No. 12 the underlined portion is randomized relative to the same portion in SEQUENCE ID No. 11, so that SEQUENCE ID No. 12 is not complementary to the ODNs of SEQUENCE ID Nos. 5–10. As is described in more detail in the experimental section below, experiments conducted in accordance with the present invention demonstrated that the ODNs of SEQUENCE ID Nos. 5–10 bind to the ODN of SEQUENCE ID No. 11 and therefore the iodobenzoyl group does not interfere with Watson Crick type hybridization. However, because these ODNs did not bind to SEQUENCE ID No. 12 (which is not complementary in the Watson Crick sense) the binding that was observed was not random or due to an artifact.

5'-CCAGCAGCCTCCCGCGACGATGCCCCTCAAC-GTTAGCTTCAC

SEQUENCE ID No. 11

5'-CCAGCAGCCTCCCGCGACGTATCTAGGGGGA-CACAGCTTCAC

SEQUENCE ID No. 12

DETAILED DESCRIPTION OF EXPERIMENTAL PROCEDURES

General Chemical Procedures.

Reverse phase HPLC analysis of nonradioactive compounds' were obtained on a Rainin pump system. Pump control and data processing used a Rainin Dynamax chromatographic software package (Macintosh). Radio-HPLC was done on a Beckman 110B pump system with an inline γ detector (Beckman Model 170. ). Retention times of the desired $^{123}$I or $^{125}$I-ODNs were verified by injection of nonradioactive standards. $T_m$ studies were performed on a Perkin Elmer Lambda 2S UV-VIS spectrophotometer equipped with a PTP6 thermal programmer. Aqueous solutions were dried at <1 Torr on a Speed Vac centrifugal evaporator (Savant Instruments, Farmingdale, N.Y.). Radiohalogenations of ODNs with $^{125}$I or $^{123}$I were carried out in a charcoal filtered plexiglass hood using standard syringe techniques. Radiochemical yields were determined using a Capintec dose calibrator.

Synthesis of Oligodeoxynucleotides.

ODNs were prepared on an Applied Biosystems Model 384 synthesizer using the 1 μmole protocols supplied by the manufacturer. Protected β-cyanoethyl phosphoramidites, CPG supports, deblocking solutions, cap reagents, oxidizing solutions, and tetrazole solutions were purchased from Glen Research (Sterling, Va.).

The 3'-hexanol modifications were introduced into ODNs of SEQUENCE ID No. 1 and SEQUENCE ID No. 2 through use of a hexanol modified CPG support. The 5'-aminohexyl modification was introduced into SEQUENCE ID No. 1 using an N-MMT-hexanolamine phosphoramidite linker (Glen Research). The 5-(3-aminopropyl)-2'-deoxyuridine modification was introduced into SEQUENCE ID No. 2 using the corresponding phthalimide protected phosphoramidite.

Characterization of Modified ODNs.

The concentrations of all ODNs were determined from the UV absorbance at 260 nm in PBS (pH 7.2). An extinction coefficient for each ODN was determined using a nearest neighbor model, (according to the teachings of Cantor et al. *Biopolymers* 9, 1059) correcting for the molecular weight of appended modifications. The value for ε was used to calculate a theoretical ratio of $A_{260}$ to concentration in μg/mL as listed in Table 1. All modified ODNs were analyzed by HPLC using a 250×4.6 mm C18 column and a gradient of 5–85% solvent B over 40 min (flow rate=1 mL/min) where solvent A=0.1M triethylammonium acetate (pH 7.5), solvent B=acetonitrile; detection was by UV absorbance at 260 nm. Retention times are listed in Table 1. ODN purity was further confirmed by polyacrylamide gel electrophoresis. PAGE was carried out under denaturing conditions (7M urea) using cross-linked 20% gels (bisacrylamide/acrylamide, 1:19; 0.4×170×390 mm) at 45 watts for 40 min. pH 8.3 TBE (100 mM tris base, 100 mM boric acid, 1 mM EDTA) was used as a running buffer. Bromophenol blue was used as a marker. The nucleotidic bands were visualized by silver staining. Unless otherwise noted, all modified ODNs were greater than 95% pure by HPLC and one major band by PAGE.

TABLE 1

Table 1. Properties of Modified ODNs

| ODN | MW | $A_{260} = 1^b$ (μg/mL) | HPLC$^c$ (min) | $T_m^d$ (°C.) |
|---|---|---|---|---|
| Sequence Id. No. 1 | 5016 | 33.1 | 8.7 | 58.8 |
| Sequence Id. No. 3 | 5409 | 35.7 | 31 | 57.4 |
| Sequence Id. No. 5 | 5246 | 34.6 | 16 | 59.6 |
| Sequence Id. No. 2 | 4880 | 34.4 | 9.0 | 57.5 |
| Sequence Id. No. 4 | 5273 | 37.1 | 23 | 48.4 |
| Sequence Id. No. 6 | 5110 | 36.0 | 11 | 55.0 |

$^b$Calculated concentration of ODN that gives 1.00 absorbance unit at 260 nm.
$^c$Elution time; C18 HPLC under conditions described above.
$^d$Determined for 2 μM solutions of modified ODN and complementary 42-mer SEQUENCE ID. No. 11.

3-(4-Tri-n-Butylstannyl)benzamidyl)-1,2-dihydro-3H-pyrrolo[3,2-e]indole-7-carboxylate Dimer Methyl Ester (Compound C)

A solution of 66 mg (0.105 mmol) of t-Boc protected 1,2-dihydro-3H-pyrrolo[3,2-e]indole-7-carboxylate dimer methyl ester (available in accordance with the literature procedure of Boger et al. *J. Org. Chem.* 1987, 52, 1521–1530 ) was stirred in 5 mL of trifluoroacetic acid for 1 h, and concentrated in vacuo to an off-white solid. The solid was dried by co-evaporation with methylene chloride (2×5 mL), and redissolved in 1 mL of methylene chloride. 100 μL of triethylamine and 70 mg (0.125 mmol) of 4-tributylstannylbenzoate 2,3,5,6-tetrafluorophenyl ester were added and the reaction mix was stirred for 3 days. 30 mL of methanol was added and the precipitated product was collected and washed with methanol. 80 mg (100% yield) of the desired product was collected. 4-Tributylstannylbenzoate 2,3,5,6-tetrafluorophenyl ester is prepared as described below.

3-(4-Tri-n-Butylstannyl)benzamidyl)-1,2-dihydro-3H-pyrrolo[3,2-e]indole-7-carboxylate Dimer 2,3,5, 6 Tetrafluorophenyl Ester (Compound A)

A suspension of 80 mg (0.105 mmol) of Compound C was stirred with 6 mL of tetrahydrofuran, 3 mL of methanol, and 1 mL of 4M lithium hydroxide. After 2 h at 45° C., the homogeneous solution was concentrated in vacuo and the resulting solid was supended in 6 mL of 1M sodium acetate (pH 7.5). The resulting acid was collected by centrifugation, washed with water, and dried in vacuo overnight. This material was dissolved in 1 mL of dimethylacetamide and treated with 200 μL of triethylamine and 100 μL of tetrafluorophenyl trifluoroacetate. (Tetrafluorophenyl trifluoroacetate is available according to the literature procedure of Gamper et al. *Nucleic Acids Res.* 21, 145–150.) After 30 min; the reaction mixture was diluted with 30 mL of methanol and 20 mL of water was used to precipitate the TFP ester. The product was collected by centrifugation, washed with 20 mL of methanol, and dried in vacuo. The crude product was purified by flash chromatography (1:1, ethyl acetate:hexanes) to give 48 mg (51% yield) of a glassy solid.

$^1$H NMR (CDCl$_3$) δ9.90 (br s, 1 H), 9.47 (s, 1 H), 8.55 (d, 1 H, J=8.7 Hz), 8.35 (br s, 1 H), 7.7–7.3 (m, 7 H), 7.08 (m, 1 H), 6.87 (s, 1 H), 4.69 (t, 2 H, J=7.4 Hz), 4.19 (br s, 2 H), 3.52 (m, 2 H), 3.30 (m, 2 H), 1.56 (m, 6H), 1.36 (m, 6 H), 1.09 (t, 6 H, J=8.4 Hz), 0.90 (t, 9 H, J=7.4 Hz).

Methyl 4-tri-n-butylstannylbenzoate

Methyl 4-bromobenzoate (5 g, 23 mmol), 5, was dissolved in anhydrous toluene (100 ml). The resulting solution was degassed by bubbling nitrogen (N$_2$) through the solution. Hexabutylditin (27.3 ml, 54 mmol) was added via syringe, followed by tetrakis(triphenylphosphine)palladium (0) (0.269 g, 0.23 mmol). The solution was refluxed under N$_2$ for 24 hours. After cooling to room temperature, the solvent was evaporated under reduced pressure to afford ~30 ml. This sample was applied to a silica gel column (45×5 cm pre-equilibrated with 100% hexanes) and eluted with 100% hexanes collecting 25 ml fractions. After eluting with 1200 ml, the column was eluted with 10% ethyl acetate/90% hexanes, collecting 25 ml fractions. Fractions which contained the product were combined, and the solvent was evaporated under reduced pressure to afford 8.6 g (88%) of the title compound.

4-Tri-n-butylstannylbenzoic acid

To a solution of methyl 4-tri-n-butylstannylbenzoate (3.0 g, 7 mmol) in absolute ethanol (60 ml) was added 0.25 g KOH (9 mmol). The resulting solution was refluxed for 2 hours. The solution was cooled and poured into an ice-cold solution of acetic acid (0.64 g, 10.6 mmol) and water (100 ml). The solution was then extracted with diethyl ether (80 ml). The ether phase was washed with water (30 ml), dried over MgSO$_4$ (5 g), filtered and evaporated under reduced pressure to afford 2.6 g (88%) of the title compound. This material was used without further purification.

N-Succinimidyl 4-tri-n-butylstannylbenzoate

To a solution of 4-tri-n-butylstannylbenzoic acid (2.0 g, 4.9 mmol) in anhydrous THF (50 ml) was added N,N'-dicyclohexylcarbodiimide (1.2 g, 5.8 mmol) followed by N-hydroxysuccinimide (0.67 g, 5.8 mmol). The resulting solution was kept at 5° C. for 18 hours. The solution was then filtered and concentrated under reduced pressure. A solution of 10% ethyl acetate/90% hexanes (25 ml) was added and the resulting solution was again filtered. The solution was concentrated to ~5 ml under reduced pressure. This material was applied to a silica gel column (19×2.5 cm, pre-equilibrated with 25% ethyl acetate/75% hexanes) and eluted with 25% ethyl acetate/75% hexanes collecting 5 ml fractions. The fractions were analyzed by HPLC to assess the purity of the samples. Fractions which were greater than 99% pure were combined. The solvents were removed under reduced pressure to afford 0.9 g (36%) of 8.

$^1$H NMR (CDCl$_3$, δ) 0.50–2.20 (m, 27H), 2.90 (s, 4H), 7.65 (d, 2H, J=8 Hz) 8.06 (d, 2H, J=8 Hz). IR (neat cm$^{-1}$) 1,780, 1,750, 1,190, 1,055, 980.

$^{13}$C NMR (CDCl$_3$ δ), 169.6, 162.6, 153.5, 137.0, 129.2, 124.5, 28.9, 27.2, 25.5, 13.5, 9.5. MS (Cl, CH$_4$) 510 (1.67%, M+1), 508 (1.34%, M+1), 452 (57.4%), 450 (43.5%), 395 (100%), 393 (75.3%), 291 (82.4%), 289 (61.7%).

2,3,5,6-tetrafluorophenyl 4-tri-n-butylstannylbenzoate

The procedure for preparing N-succinimidyl 4-tri-n-butylstannylbenzoate was used except that 2,3,5,6-tetrafluorophenol was used in place of N-hydroxysuccinimide. The TFP ester was isolated as a colorless liquid.

$^1$H NMR (CDCl$_3$) δ 8 8.12 (d, 2H, J=8 Hz), 7.67 (d, 2H, J=8 Hz), 7.04 (m, 1H), 1.56 (m, 6H), 1.36 (m, 6H), 1.12 (t, 6H, J=8.3 Hz), 0.90 (t,9H, J=7.1 Hz).

5'-Aryl Sn-ODN, SEQUENCE ID No. 3

To 0.50 mg (0.10 µmol) of ODN of SEQUENCE ID No. 1 in 0.13 mL of water was added 0.1 mL of 1M sodium borate buffer (pH 8.3) and 0.3 mL of 0.1M sodium borate buffer (pH 8.3) in a 1.7 mL eppendorf tube. A solution of 5 mg (10 µmol) of N-hydroxysuccinimidyl 4-tri(n-butyl) stannylbenzoate in 0.5 mL of THF was added, and the milky emulsion was shaken for 16 h. The mixture was concentrated to a volume of approximately 0.1 mL on a Speed Vac to remove THF. The cloudy solution was dissolved in 0.4 mL of 0.1M TEAA (pH 7.5) and filtered through a 0.45 µm filter. The filter was rinsed with an additional 0.2 mL of buffer, and the combined filtrate was purified by HPLC using the conditions described in FIG. 2. The desired product (31 min peak) was collected and 0.1 mL of 1M borate buffer (pH 8.3) was added before taking to dryness on a Speed Vac. The white solid product was reconstituted with 0.5 mL of water and the concentration was determined by $A_{6260}$ measurement. Recovery of the ODN of SEQUENCE ID No. 3 was 0.23 mg (42% yield).

5'-Modified $^{127}$I-ODN, SEQUENCE ID No. 5
Method A.

To a solution of 5.4 µg (1 nmol) of 5'-Aryl Sn-ODN of SEQUENCE ID No. 3 in 12 µL of water was added 7.5 µL (5 nmol) of a 0.1 mg/mL solution of sodium iodide and 6.9 µL of 0.1M borate buffer (pH 8.3). Reaction was initiated by adding 4.56 µL (20 nmol) of a 1 mg/mL solution of chloramine T hydrate (ChT) in water. After 5 min, the reaction was quenched with 5 µL of 10 mg/mL solution of sodium bisulfite. The reaction was analyzed by HPLC and showed complete conversion of the 5'-Aryl Sn-ODN of SEQUENCE ID) No. 3 (31 min) to the desired product 5'-Modified $^{127}$I-ODN, SEQUENCE ID No. 5 (16min).
Method B.

To 0.50 mg (0.10 µmol) of ODN of SEQUENCE ID No. 1 in 0.127 mL of water was added 0.1 mL of 1M sodium borate buffer (pH 8.3), 0.3 mL of 0.1M sodium borate buffer (pH 8.3) in a 1.7 mL eppendorf tube. A solution of 4-iodobenzoyl chloride (2.5 mg, 9.4 µmol) in 0.5 mL of THF was added and the solution was kept at room temperature for 16 h. C18 HPLC showed complete reaction of the ODN of SEQUENCE ID No. 1 (8.7 min). The reaction mixture was diluted to 2 mL and purified by centrifugal ultrafiltration through a 1000 MW cutoff concentrator (Filtron). This process removed excess hydrolyzed acid chloride and gave the desired product SEQUENCE ID No. 5 in 97% purity. The retentate was diluted to 0.5 mL with water and concentration was determined by $A_{260}$ measurement. Recovery of SEQUENCE ID No. 5 was 0.41 mg (77% yield). This product co-eluted with ODN prepared by Method A, and was used for thermal denaturation experiments.

Internally Modified Aryl Sn-ODN SEQUENCE ID No 4

To 0.49 mg (0.10 µmol) of vacuum dried ODN of SEQUENCE ID No. 2 in a 1.7 mL eppendorf tube was added 0.5 mL of dry DMSO. After shaking 15 min, triethylamine (50 µL, 0.36 mmol) and N-hydroxysuccinimidyl 4-tri(n-butyl)stannylbenzoate (1.8 mg, 3.6 µmol) were added. The mixture was shaken for 16 h, then concentrated for 1 h to remove triethylamine. The ODN product was precipitated by adding to 5 mL of 2% LiClO$_4$ in acetone. After centrifuge, the pellet was washed with acetone (sonicated), re-centrifuged, and dried in vacuo. The pellet was dissolved in 0.2 mL of water and purified by HPLC using the conditions described in FIG. 2. HPLC indicated unreacted ODN of SEQUENCE ID No. 2 at 9 min (63 area %) and the desired product at 23 min (34 area %). The desired fraction was collected and 0.02 mL of 1M borate buffer (pH 8.3) was added before taking to dryness on the Speed Vac. The white solid product was reconstituted with 0.2 mL of water and the concentration was determined by $A_{260}$ measurement. Recovery of SEQUENCE ID No 4 was 0.13 mg (24% yield).

Internally Modified $^{127}$I-ODN of SEQUENCE ID No. 6
Method A.

To a solution of 5.3 µg (1 nmol) of Aryl Sn-ODN of SEQUENCE ID No 4 in 19 µL of water was added 7.5 µL (5 nmol) of a 0.1 mg/mL solution of sodium iodide and 6.9 µL of 0.1M borate buffer (pH 8.3). Reaction was initiated by adding 4.56 µL (20 nmol) of a 1 mg/mL solution of ChT in water. After 5 min, the reaction was quenched with 5 µL of 10 mg/mL solution of sodium bisulfite. The reaction was analyzed by HPLC and showed complete conversion of Aryl Sn-ODN SEQUENCE ID No 4 (23 min) to the desired product $^{127}$I-ODN of SEQUENCE ID No. 6 (11 min).
Method B.

To 0.5 mg (0.1 µmol) of vacuum dried ODN of SEQUENCE ID No. 2 in a 1.7 mL eppendorf tube was added 0.5 mL of dry DMSO, triethylamine (50 µL, 0.36 mmol) and 4-iodobenzoyl chloride (4 mg, 15 µmol). The mixture was shaken for 16 h and the ODN product was precipitated by adding to 5 mL of 2% LiClO$_4$ in acetone. After centrifuge, the pellet was washed with acetone (sonicated), re-centrifuged, and dried in vacuo. The pellet was dissolved in 0.2 mL of water and purified by HPLC. The desired product (10.7 min peak) was collected and taken to dryness on the Speed Vac. The white solid product was reconstituted with 0.2 mL of water and the concentration was determined by $A_{260}$ measurement. Recovery of $^{127}$I-ODN of SEQUENCE ID No. 6 was 0.12 mg (23% yield). This product co-eluted with ODN prepared by Method A, and was used for thermal denaturation experiments.

Thermal Denaturation Studies.

The melting temperatures ($T_m$) of all modified ODNs were determined. Selected ODNs were prepared in 2 μM concentrations as solutions in pH 7.2 PBS (9.2 mM disodium phosphate, 0.8 mM monosodium phosphate, 0.131M sodium chloride). Thermal dissociation curves were obtained by heating samples from 10 to 90° C. with a temperature increase of 0.5° C./min. $A_{260}$ vs. time and the first derivative data were determined automatically. The $T_m$ was determined from the derivative maximum. Data from one representative run is given in Table 1.

Conversion of 5'-Aryl Sn-ODN of SEQUENCE ID
No. 3 to $^{125}$I-ODN SEQUENCE ID No. 7

To a solution of 11 μg (2 nmol) of 5'-Aryl Sn-ODN of SEQUENCE ID No. 3 in 22 μL of 0.1M borate buffer was added 1.41 mCi (approximately 560 pmol) of Na$^{125}$I in 3 μL of 0.1M NaOH (New England Nuclear, Mass.) and 20 μg (88 nmol) of ChT in 20 μL of water. After 15 min, the reaction was quenched with 10 μL of a 10 mg/mL solution of sodium bisulfite. Radio-HPLC analysis showed 69% conversion of $^{125}$I to the desired I-ODN. The $^{125}$I-ODN was purified on a Poly-Pak reverse phase syringe cartridge (Glen Research) which had been pre-equilibrated with 0.1M TEAA buffer. The crude reaction mix was added to the top of the column and eluted with 2 mL of TEAA and 2 mL of 20% acetonitrile in TEAA. Fractions of approximately 0.5 mL were collected and each was measured in the dose calibrator. The most concentrated fraction (#5) contained 0.384 mCi (27% radiochemical yield) of $^{125}$I-ODN of SEQUENCE ID No. 7. Radio-HPLC analysis of this sample showed 96% purity. Conversion of 5'-Aryl Sn-ODN of SEQUENCE ID No. 3 to $^{123}$I-ODN of SEQUENCE ID No. 8

To a solution of 11 μg (2 nmol) of 5'-Aryl Sn-ODN of SEQUENCE ID No. 3 in 24 μL of 0.1M borate buffer was added 5.07 mCi (approximately 21 pmol) of Na$^{123}$I in 20 μL of 0.1M NaOH (Nordion International, Vancouver B.C.). The mixture was neutralized with 3 μL of 1N acetic acid using a 25 μL syringe and reaction was started by adding 10 μg (44 nmol) of ChT in 10 μmL of water. After 5 min, the reaction was quenched with 10 μL of a 10 mg/mL solution of sodium bisulfite. The reaction mixture was injected on a 4.6×150 mm PRP-1 HPLC column and the desired $^{123}$I-ODN product was collected in approximately 1.7 mL of buffer (gradient described above) γ detection showed 30% conversion of Na$^{123}$I to the desired $^{123}$I-ODN SEQUENCE ID No. 8 that eluted with a retention time of 14.9 min. Measurement of the collected fraction in the dose calibrator showed 1.42 mCi (28% radiochemical yield). The fraction was concentrated by centrifugal ultrafiltration through two 3000 MW cut-off concentrators (Filtron) to a volume of approximately 0.4 mL (70 min @ 7000 rpm). Further desalting was accomplished by combining the retentates, diluting with 1 mL of water and re-concentrating to give 0.75 mCi of SEQUENCE ID No. 8 (specific concentration= 32.5 μCi/10 μL). Radio-HPLC analysis of this sample showed 100% purity.

Conversion of Aryl Sn-ODN SEQUENCE ID No 4
to $^{123}$I-ODN of SEQUENCE ID No. 10

To a solution of 11 μg (2 nmol) of Aryl Sn-ODN SEQUENCE ID No 4 in 37.8 μL of 0.1M borate buffer was added 5.35 mCi (approximately 22 pmol) of Na$^{123}$I in 19 μL of 0.1M NaOH. The mixture was neutralized with 3 μL of 1 N acetic acid and reaction was started by adding 10 μg (44 nmol) of ChT in 10 μL of water. After 5 min, the reaction was quenched with 10 μL of a 10 mg/mL solution of sodium bisulfite. The reaction mixture was injected on PRP-1 HPLC as described above, and the desired $^{123}$I-ODN of SEQUENCE ID No. 10 eluted with a retention time of 13.0 min in approximately 1.5 mL of buffer. Measurement of the collected fraction in the dose calibrator showed 1.17 mCi (22% radiochemical yield) of $^{123}$I-ODN of SEQUENCE ID No. 10. The recovered activity was concentrated by centrifugal ultrafiltration through two 3000 MW cut-off concentrators (Centricon) for 45 min at 7000 rpm. Further desalting was accomplished by diluting each retentate with 1 mL of water and reconcentrating. The retentates were combined and concentrated to the deadstop volume to give 0.49 mCi of $^{123}$I-ODN of SEQUENCE ID No. 10 (specific concentration=81.6 μCi/10 μL).

Polyacrylamide Gel Electrophoresis Assays
(General Procedures).

The 42-mer ODN targets (complementary ODN of SEQUENCE ID No. 11 or random ODN of SEQUENCE ID No. 12) were purified by gel electrophoresis prior to 5'-$^{32}$p labeling by treatment with $^{32}$P-γ-ATP using polynucleotide kinase. Each ODN (10 pmol) was labeled and concentrations were determined by assuming complete recovery of ODN following purification through a gel filtration column: ODN 4=45 fmol/μL, ODN 5=39 fmol/μL. The specific concentration (μCi/μL) of the $^{123}$I-ODN solutions were determined immediately before incubation with the appropriate $^{32}$p labeled ODN target. $^{123}$I-ODN concentrations (fmol/μL) were determined using a specific activity of 240 Ci/μ mol. After complete decay of the $^{123}$I (1 week), the $^{32}$P targets were analyzed by PAGE.

Gel Retardation Assay of $^{123}$I-ODN of
SEQUENCE ID No. 8; nondenaturing PAGE

The hybridization properties of $^{123}$I-ODN of SEQUENCE ID No. 8 were determined by incubating 32.5 μCi (137 fmol) with 100 fmol of $^{32}$P labeled ODN of SEQUENCE ID No. 11 or with ODN of SEQUENCE ID No. 12 in 100 μL of phosphate buffered saline (pH 7.2). Unlabeled target ODNs were added to give various ratios of I-ODN to target ODN. The ratio of $^{123}$I-ODN to ODN SEQUNCE ID No. 11 were either 1.37:1, 0.34:1 or 1.37:1 with 100 fold excess of random ODN of SEQUENCE ID No. 12. Control mixtures had either no I-ODN or no complementary target. After 1 week at room temperature, the $^{32}$p labeled ODN targets were analyzed by non-denaturing PAGE. A 5 μL aliquot of each hybridization solution was mixed with 5 μL of loading buffer (0.25% bromophenol blue, 0.25% xylene cyanol FF, and 20% Ficoll in water). Each sample was loaded on an 8% gel (160×160×0.4 mm) which was poured and cooled overnight at 10° C. The gel was run at 10 W for 2.75 h using pH 8.3 TBE (100 mM tris base, 100 mM boric acid, 1 mM EDTA) as a running buffer. The gel was dried, and radioactive bands corresponding to either dsDNA or ssDNA were visualized by autoradiography. The results of this PAGE analysis show that the radioiodinated ODN of SEQUENCE ID No. 8 hybridizes with the complementary ODN of SEQUENCE ID No. 11, but not with the random ODN of SEQUENCE ID NO. 12.

What is claimed is:

1. A process for preparing a halogenated oligonucleotide, having the formula (i) or (ii)

[Ψ—ARYL—Y—Z—Y']$_p$—ODN     (i)

[Ψ—C(R$_2$)=C(R$_2$)—Y—Z—Y']$_p$—ODN     (ii)

where ODN represents an oligonucleotide;

Ψ represents a halogen atom;

p is an integer having the value of 1 to 30 with the proviso that the value of p does not exceed the number of nucleotide units in the ODN;

ARYL represents a benzene, naphthalene, pyridine, pyrrol, thiophene, or furan ring which may optionally be substituted with 1, 2, or 3 R$_3$ groups;

R$_2$ is H or R$_3$;

R$_3$ is alkyl or cycloalkyl of 1 to 5 carbons, or is alkoxy having 1 to 5 carbons, , alkylthio having 1 to 5 carbons or alkylamino having 1 to 5 carbons, or dialkylamino where each alkyl group independently has 1 to 5 carbons;

Y is a linker arm that covalently links the Z moiety to the ARYL or to the C(R$_2$)=C(R$_2$) moiety, the length of said Y group not exceeding the length of a normal alkyl chain of 25 carbons;

Y' is a linker arm that covalently links the Z moiety to the ODN, the length of said Y group not exceeding the length of a normal alkyl chain of 25 carbons, and Z is a moiety formed by the reaction between an electrophilic and a nucleophilic reactive group;

the process comprising the steps of (1) reacting a trialkylstannyl oligonucleotide of the formula (iii) or (iv)

[(R$_1$)$_3$Sn—ARYL—Y—Z—Y']$_p$—ODN     (iii)

[(R$_1$)$_3$Sn—C(R$_2$)=C(R$_2$)—Y—Z—Y']$_p$—ODN     (iv)

where R$_1$ is an alkyl or cycloalkyl group having 1 to 10 carbons and the remaining symbols are defined as above, with an electrophilic halogen Ψ+, and thereafter (2) separating the halogenated oligonucleotide of formula (i) or (ii) from the trialkylstannyl oligonucleotide of formula (iiii) or (iv).

2. The process of claim 1 where the step of separating is performed on a reverse phase column and wherein the halogenated oligonucleotide of formula (i) or (ii) is eluted from the column before the trialkylstannyl oligonucleotide of formula (iii) or (iv).

3. The process of claim 2 wherein the step of separating is performed with a gradient of a less polar solvent added to an aqueous solvent.

4. The process of claim 2 wherein the step of separating is performed by eluting the halogenated oligonucleotide with a polar solvent that is incapable of removing the trialkylstannyl oligonucleotide from the column.

5. The process of claim 4 wherein the step of separating is performed on a disposable syringe cartridge column.

6. The process of claim 1 further comprising the step of reacting a trialkylstannyl reagent of formula (v) or (vi)

X—Y—ARYL—Sn(R$_1$)$_3$     (v)

X—Y—C(R$_2$)=C(R$_2$)—Sn(R$_1$)$_3$     (vi)

with an oligonucleotide of formula (vii)

ODN—(Y'—X')$_p$ (vii)

where, X and X' are reactive groups that are capable of reacting with one another to form the Z moiety, and the remaining symbols are defined above, to provide by said reaction the trialkylstannyl oligonucleotide of formula (iii) or (iv).

7. The process of claim 6 where the trialkylstannyl reagent has the formula (v).

8. The process of claim 7 where $R_1$ is n-butyl.

9. The process of claim 8 where in the trialkylstannyl reagent (v) the ARYL group is phenyl, substituted in the 1 and 4 (para) positions by the X—Y and Sn($R_1$)$_3$ groups.

10. The process of claim 9 where the trialkylstannyl reagent (v) is an active ester of 4-tri(n-butyl)stannylbenzoic acid.

11. The process of claim 9 where the reagent (v) is selected from N-hydroxysuccinimidyl 4-tri(n-butyl)stannylbenzoate, and 3-(4-tri-n-butylstannyl)benzamidyl)-1,2-dihydro-3H-pyrrolo[3,2-e]indole-7-carboxylate dimer 2,3,5,6 tetrafluorophenyl ester.

12. The process of claim 7 where p is 1 or 2 and the [Ψ'—ARYL—Y—Z—Y'] group is attached to a terminal phosphate of the oligonucleotide.

13. The process of claim 7 where the [Ψ'—ARYL—Y—Z—Y'] group is attached to a heterocyclic base of the oligonucleotide.

14. The process of claim 1 where the halogen Ψ is radioactive iodine.

15. The process of claim 14 where the halogen is $^{125}$I or $^{123}$I.

16. An oligonucleotide of the formula (i) or (ii) as defined in claim 1, having essentially isotopically pure $^{123}$I as the halogen Ψ, said oligonucleotide having been prepared in accordance with the process of claim 1.

17. A process of claim 1 where Z is selected from the groups (1) —CO—NH—

(2) —(2)—NH—CO—NH—;

(3) —(3)—NH—CS—NH—;

(4) NH—CO—CH$_2$—S—, and

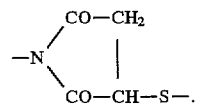
(5)

18. An oligonucleotide which has the formula selected from

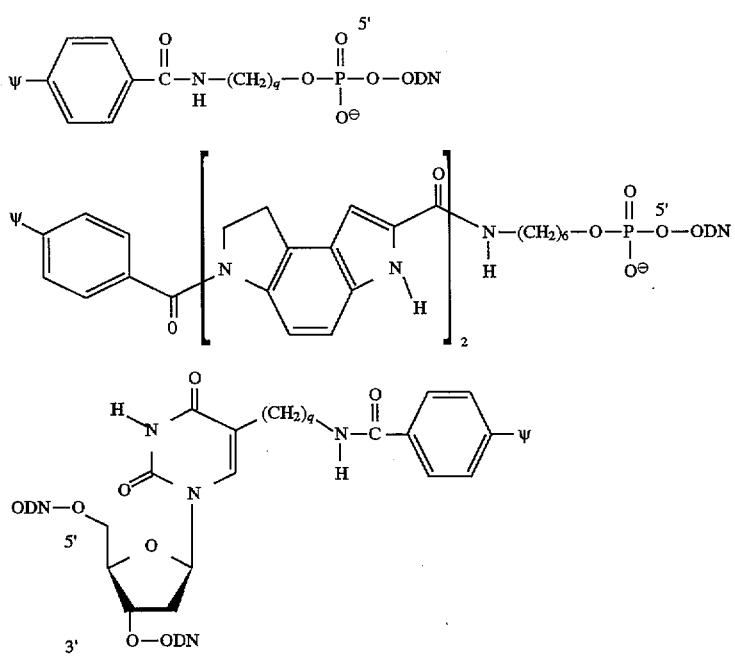

where q is an integer from 1 to 10, said oligonucleotide having been prepared in accordance with the process of claim 1.

19. An oligonucleotide in accordance with claim 18 wherein Ψ is essentially isotopically pure $^{123}$I.

20. A process for preparing a halogenated oligonucleotide having the formula (viii)

[Ψ—C$_6$H$_4$—Y—CO—NH—Y+]$_p$—ODN (viii)

where ODN represents an oligonucleotide;

Ψ represents a halogen atom;

p is an integer having the value of 1 to 30 with the proviso that the value of p does not exceed the number of nucleotide units in the ODN;

Y represents a direct valence bond between the C$_6$H$_4$ and CO groups or Y represents the divalent group

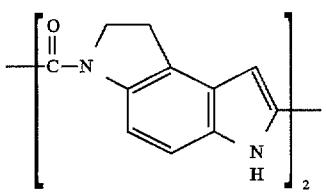

and

Y' represents —(CH$_2$)$_q$— where q is an integer between 1 to 10, the process comprising the steps of (1) reacting a trialkyl stannyl reagent of the formula (ix)

$$(R_1)_3Sn—C_6H_4—Y—CO—X \qquad (ix)$$

where R$_1$ is an alkyl or cycloalkyl group having 1 to 10 carbons and X is selected from N-succinimidyloxy and 2,3,5,6-tetrafluorophenyloxy, with an oligonucleotide of the formula (x)

$$[H_2N—Y']_p—ODN \qquad (x)$$

to obtain a trialkylstannyl oligonucleotide of the formula (xi)

$$[(R_1)_3Sn—C_6H_4—Y—CO—NH—Y']_p—ODN \qquad (xi),$$

(2) reacting the trialkylstannyl oligonucleotide of the formula (xi) with an electrophilic halogen Ψ+, and thereafter (3) separating the halogenated oligonucleotide of formula (viii) from the trialkylstannyl oligonucleotide of formula (xi), said step of separating being performed on a reverse phase column and wherein the halogenated oligonucleotide of formula (viii) is eluted from the column before the trialkylstannyl oligonucleotide of formula (xi).

21. The process of claim 20 where R$_1$ is n-butyl.

22. The process of claim 21 where Y represents a direct valence bond.

23. The process of claim 20 where p is 1, and the NH—Y' group is connected to a terminal phospate of the oligonucleotide.

24. The process of claim 23 where Y' is —(CH$_2$)$_6$—.

25. The process of claim 20 where the NH—Y' group is connected to a heterocyclic base of the oligonucleotide.

26. The process of claim 25 where the NH—Y' group is connected to the 5 position of a 2'-deoxyuridine moiety of the oligonucleotide.

27. The process of claim 20 where the halogen is $^{125}$I or $^{123}$I and where the step of reacting with the electrophilic halogen Ψ+ comprises reacting the trialkylstannyl oligonucleotide of formula (xi) with a salt of $^{125}$iodine or $^{123}$iodine in the presence of an oxidizing agent.

28. The process of claim 27 wherein the step of separating is performed on a disposable syringe cartridge column.

29. An oligonucleotide of formula (viii) having been prepared in accordance with the process of claim 28.

30. An oligonucleotide of formula (viii) having been prepared in accordance with the process of claim 28 wherein the halogen Ψ is essentially isotopically pure $^{123}$I.

* * * * *